United States Patent [19]

Ross, Jr. et al.

[11] 4,211,623
[45] Jul. 8, 1980

[54] HALIDE ELECTRODE

[75] Inventors: James W. Ross, Jr.; Charles E. Amass, both of Cambridge; Charles S. Baer, Lynn; Martin H. Thomae, Watertown, all of Mass.

[73] Assignee: Orion Research Incorporated, Cambridge, Mass.

[21] Appl. No.: 973,567

[22] Filed: Dec. 27, 1978

[51] Int. Cl.² .................. G01N 27/30; B22F 3/02
[52] U.S. Cl. .................. 204/195 M; 204/195 H; 264/111
[58] Field of Search .......... 204/195 M, 1 B, 195 H, 204/295; 324/29; 264/111; 29/592

[56] References Cited

U.S. PATENT DOCUMENTS

| 3,563,874 | 2/1971 | Ross et al. | 204/195 M |
| 3,824,169 | 7/1974 | van Osch et al. | 204/195 M |

OTHER PUBLICATIONS

D. J. G. Ives et al., "Reference Electrodes, Theory and Practice," pp. 127–178, (1961).
Josef F. Lechner et al., Electroanal. Chem. & Interfacial Electrochem., vol. 57, pp. 317–323, (1974).
Paul K. C. Tseng et al., Analytical Letters, vol. 9, No. 9, pp. 795–805, (1976).
Ivan Sekerka et al., J. Electroanal. Chem., vol. 57, p. 317, (1974).
G. B. Marshall et al., Analyst, vol. 103, pp. 438–446, May 1978.
U. Hannema et al., Z. Anal. Chem., vol. 250, pp. 302–306, (1970).

*Primary Examiner*—G. L. Kaplan
*Attorney, Agent, or Firm*—John B. Miller

[57] ABSTRACT

An electrode sensitive to halide ion $X^-$ in solution, the ion-sensitive portion being an imporous membrane of a solid amalgam, such as gold and mercury, in combination with a finely divided salt of mercurous and halide ion $X^-$, e.g. of the form $Hg_2Cl_2$.

11 Claims, 23 Drawing Figures

EFFECT OF CHANGE IN AMALGAM COMPOSITION (75% $Hg_2Cl_2$)

EFFECT OF CHANGE IN % MERCUROUS CHLORIDE

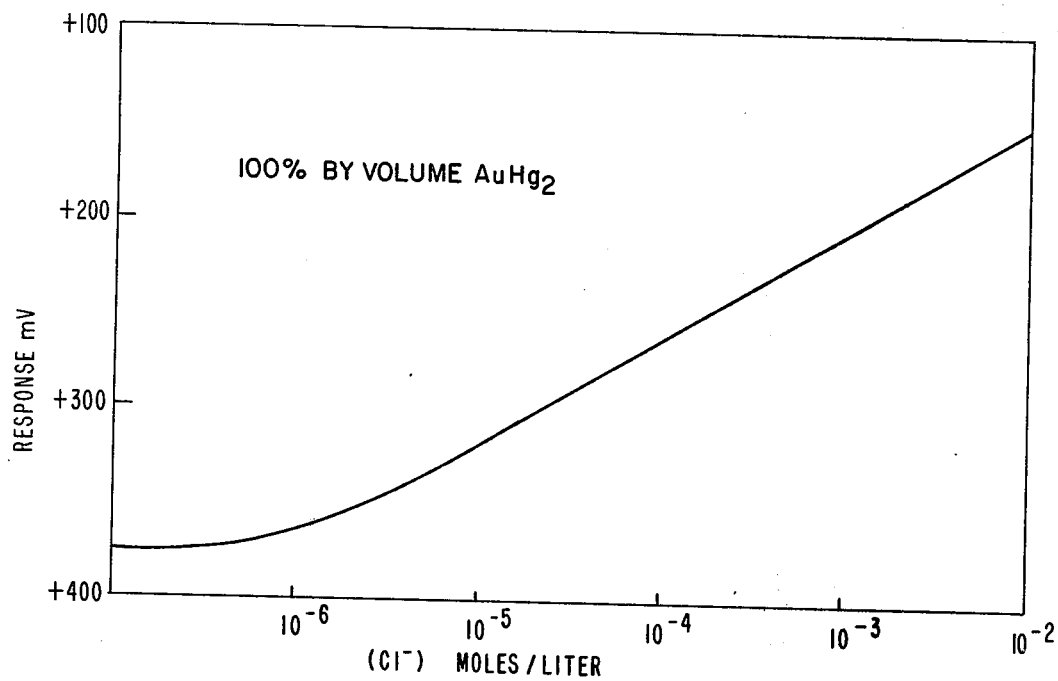
FIG. 6a
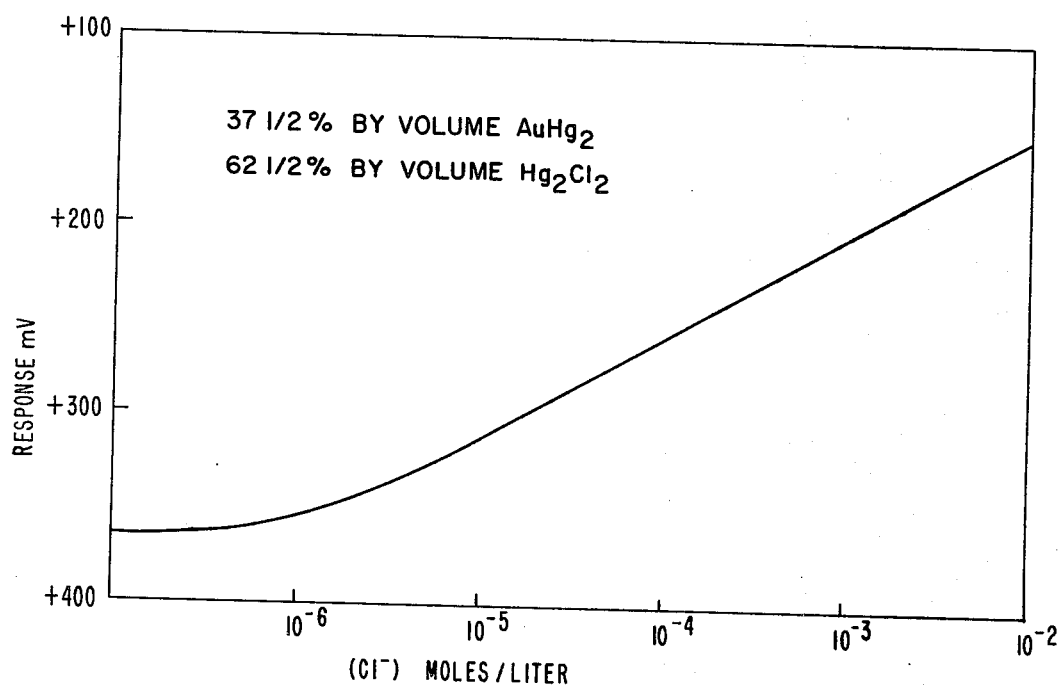
FURTHER EXAMPLES FIG. 6b

CALIBRATION OF
MERCUROUS BROMIDE
AMALGAM ELECTRODES

CALIBRATION OF MERCUROUS IODIDE
AMALGAM ELECTRODES

HALIDE ELECTRODE

BACKGROUND OF THE INVENTION

1. Field of Invention

This invention relates to potentiometer detection and measurements, and more particularly to the detection and measurement of halide ions, including chloride ion, $Cl^-$, bromide ion, $Br^-$, and iodide ion, $I^-$.

2. Prior Art Statement:

The standard mercury pool calomel electrode has been known since 1890, when it was introduced by Ostewald. The history, theory, and operation of this electrode are amply set forth in *Reference Electrodes, Theory and Practice*, edited by Ives and Janz, 1961, Chapter 3. The construction of this electrode consists in part of placing calomel (mercurous chloride, $Hg_2Cl_2$) on top of a mercury pool. By placing an internal electrolyte, such as concentrated KCl or the like in contact with the pool and the calomel, a standard calomel reference electrode is created. By using the solution of interest as the internal electrolyte, a variable potential electrode is set up, but the use of such electrodes has not been widespread. (See, *Reference Electrodes*, Ch. 3, supra). The central and pervasive limitation of this electrode, together with its bromide ion and iodide ion counterparts, is structural: the liquid mercury pool makes ion-selective use of this electrode extremely difficult.

A substantially different approach to measurement of chloride ion, bromide ion, and iodide ion has been disclosed by Ross, et al in U.S. Pat. No. 3,563,874, issued Feb. 16, 1971. In this patent, a substantially imporous membrane of a mixture of silver sulfide and a silver halide selected from the group consisting of silver iodide, silver bromide and silver chloride was disclosed to be selectively sensitive to the respective halide ions.

J. Sekerka and J. F. Lechner in *J. Electroanal. Chem.*, 57, 317 (1974) describe a chloride ion-selective electrode having an active membrane composed of a mixture of mercuric sulfide, HgS, and mercurous chloride, $Hg_2Cl_2$ (calomel). A near parallel effort by Paul K. C. Tseng and W. F. Gutnecht as described in *Analytical Letters*, 9 (9) 795-805 (1976) has resulted in the production of a bromide ion-selective electrode having an active membrane composed of HgS and $Hg_2Br_2$. See also, J. Sekerka and J. F. Lechner, *J. Electroanal. Chem.*, 69, 339 (1976). More recently, G. B. Marshall and D. Midgley have described a solid state chloride ion selective electrode with a membrane composed of a compressed mixture of mercury (II) sulphide and mercury (I) chloride, Analyst, May, 1978, Vol. 103 p. 438. This electrode has been found suitable for determining chloride at concentrations as low as $10^{-7}$ mol/1.

V. Hannema, G. J. van Rossum, and G. den Boef published a paper in November, 1970 *On the Use of the Mercury Electrode in Chelatometric Potentiometers Titrations*, Z. Anal. Chem., 250, 302-306 (1970). A mercury electrode is described in the form of a solid gold rod. The rod is covered with plastic tubing except at the ends. The lower end is covered with mercury and the electric connection is made at the other end. Before every titration the mercury electrode is superficially cleaned with 14 M $HNO_3$, rinsed with water, re-coated with mercury by dipping it into metallic mercury, rinsed with water, dipped into 0.1 M EDTA and again rinsed with water. The Hannema electrode is sensitive to mercury ion concentrations, not chloride ions. The Hannema electrode, in sharp contrast to the present invention, is not formed of any intimate mixture of gold, mercury, and mercurous halide salt. As a result, perennial cleaning and re-coating with mercury prior to each determination of mercury metal ions is required.

SUMMARY OF THE INVENTION:

One object of the invention is to provide an ion sensitive electrode with Nernstian response to changes in concentration of any of the group of halide ions including chloride ion, bromide ion, and iodide ion, to concentration levels in the range of 1 ppb. Another object of the invention is to provide a membrane that is sensitive to halide ions from the group including chloride ion, bromide ion, and iodide ion.

The objects of the invention are effected by providing an ion-selective membrane composed of a mixture of a solid amalgam of gold and mercury with a finely divided mercurous halide (X) salt, in the form $Au_yHg_z/Hg_2X_2$. The mixture is compressed with sufficient force to render it a substantially imporous mass. Electrical contact with one surface of the membrane is established at a substantially fixed potential. By using mercurous chloride, mercurous bromide, or mercurous iodide as the mercurous halide salt, membranes sensitive to chloride ion, bromide ion, and iodide ion respectively are constructed.

BRIEF DESCRIPTION OF THE DRAWINGS:

For a more full understanding of the nature and objects of the present invention, reference should be made to the following detailed description taken in connection with the accompanying drawings wherein.

Figure 1:
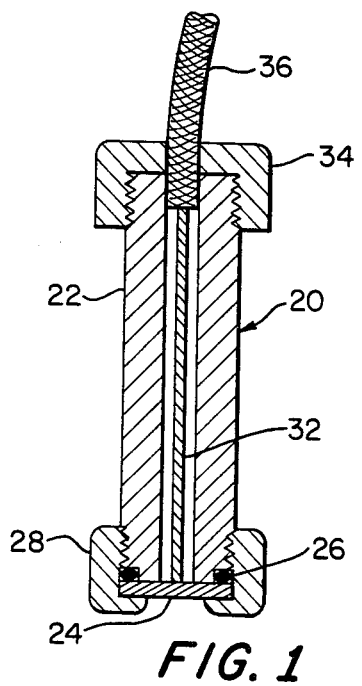
FIG. 1 is a schematic cross-sectional view of an electrode illustrating the principles of the invention.

DETAILED DESCRIPTION OF THE INVENTION:

Referring now to the drawings there is shown in FIG. 1, electrode 20 embodying the principles of the present invention and comprising support and enclosure means securely in the form of an elongated, hollow tubular container 22. The container typically is formed of a liquid-impervious, substantially rigid, electrically insulating material such as unplasticized polyvinyl chloride, polytetrafluouroethylene epoxy resins or the like, substantially chemically inert to aqueous solutions containing chloride, bromide or iodide ions.

One end of container 22 is sealed with a barrier or membrane 24, such as a thin, imporous disk, formed of a mixture of a solid amalgam of gold and mercury and a mercurous halide selected from the group consisting of mercurous chloride $Hg_2Cl_2$, mercurous bromide $Hg_2Br_2$, and mercurous iodide, $Hg_2I_2$. The term "membrane", as used herein, consistent with its use in potentiometric technology generally, is intended to include structures, generally regardless of size or curvature, which provide a pair of limiting surfaces across which ionic charge transfer is effected. The thickness of the membrane is important only in respect to its mechanical strength and, of course, the electrical resistance across it. Typically the membrane thickness is on the order of 0.08 inches. Membrane 24 can be sealed to container 22 by suitable water-insoluble, electrically insulating adhesives such as epoxy resins or the like. Alternatively, the membrane, as shown in FIG. 1, can be disposed across an end of container 22 on o-ring 26, and held compressed against the o-ring by collar 28, threadedly mounted on the container.

Means are provided for forming an electrical contact at a fixed or reference potential at the surface of membrane 24 facing the interior of container 22. To this end electrode 20 includes contact wire 32, which can be conveniently a silver or platinum wire or the like, securely attached to the interior face of membrane 24 to provide good electrical contact. The other end of container 22 is fitted with apertured cap 34 through which extends the usual coaxial cable 36, the center conductor of which is connected to contact wire 32 and the peripheral conductor of which provides desirable shielding by being typically grounded.

The most important consideration with respect to the electrode of FIG. 1 lies in the nature of membrane 24. The latter is an intimate mixture of an amalgam of gold and mercury and a mercurous halide. The composition of the amalgam in terms of ratios of gold to mercury, as well as the proportions of amalgam to mercurous halide can vary quite widely. The method of formation of the membrane is also an important element of the invention.

The membrane of the present invention is formed by compressing finely divided, intimately mixed, mercury-gold amalgam and mercurous halide under high enough pressure to compact the mixture into a substantially imporous mass. The preferred method of preparing the mixture is to coprecipitate the various ingredients in the desired ratios so as to obtain an extremely intimate homogeneous mixture. For example to obtain the coprecipitate for the chloride ion sensitive membrane, appropriate quantities of solutions of chloroauric acid $HAuCl_4$, calomel $Hg_2Cl_2$, and chromous chloride (reducing agent) $CrCl_2$ are mixed together. The relative quantities of chloroauric acid, chromous chloride and calomel are varied according to the desired proportion of gold Au and mercury Hg sought in the amalgam and according to the desired proportion of amalgam sought in the full precipitate. The preferred forms permit proportional variation in both the composition of the Au.Hg amalgam and in the amalgam/calomel mixture. Operational electrodes have been constructed from amalgam compositions ranging from pure gold to $AuHg_2$ ($\frac{2}{3}$mercury). The latter composition is shown by the phase diagram in FIG. 9 to be the point at which gold and mercury cease to coexist as a solid amalgam. In addition to permitted variations in the amounts of gold and mercury in the amalgam, the percentage of amalgam can also be varied within the range of 85% calomel/15% amalgam by volume to 0% calomel/100% amalgam. If the percentage of calomel in the mixture is higher than about 85%, the conductivity of the material upon being pressed into the membrane is so poor that the membrane essentially acts within the electrode as an open circuit. The range of amalgam compositions and range of amalgam/mercurous salt mixtures utilized in constructing the membranes are summarized in FIG. 3. However, applicant does not claim pure gold.

Whatever the choice of amalgam composition and mixture composition, the resulting $Hg_2Cl_2$/AuHg mixture is thoroughly washed with dilute $10^{-3}$ M perchloric acid $HClO_4$, and dried in a vacuum oven at 40° C. for two hours. The dried precipitate is then packed into a die and compressed at room temperature for a few minutes, typically at ram pressures of 10,000 psi/in$^2$. The die used is about 0.312 inch in diameter and provides sufficient depth so that the dried mixture can be compressed to form a pellet of the desired thickness, e.g., 0.08 inch. The precise molecular stucture of the AuHg amalgam/merucrous chloride membrane is not known with certainty. However, it is believed that mercury is present in the membrane at a constant level.

Membranes can be similarly prepared for bromide ion and iodide ion electrodes by substituting mercurous bromide, $Hg_2Br_2$, or mercurous iodide $Hg_2I_2$ for mercurous chloride $Hg_2Cl_2$. In all cases the membranes are substantially imporous, mechanically very strong, highly water-insoluble materials. The term "highly water-insoluble" used herein indicates that the membrane material has a solubility when in equilibrium with an aqueous solution in contact therewith, such that in that solution the concentration or activity of halide ions derived from the membrane is less than the lowest halide ion activity that one can reasonably expect or intends to measure in the solution.

Figure 2:
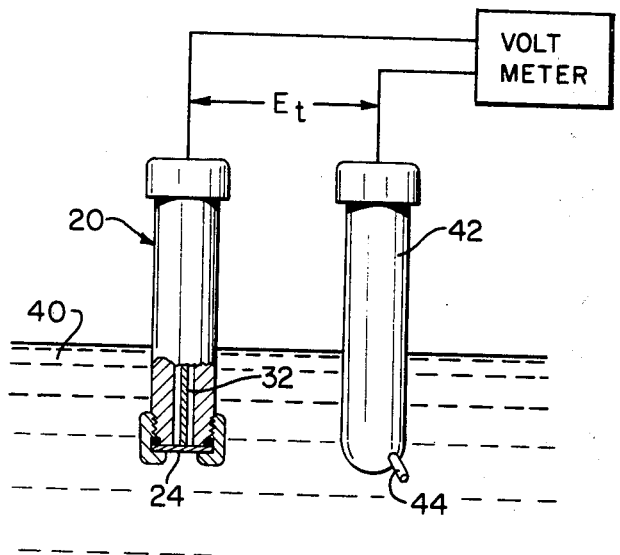
FIG. 2 is a schematic view, partly in cross section, of a system employing the electrode of FIG. 1 for the detection of halide ions in solution.

Referring now to FIG. 2, electrode 20 is shown in use in test solution 40, with the exterior surface of membrane 24 in contact therewith. Test solution 40 is a solution containing or which is thought to contain halide ions whose detection and determination is sought. A standard reference electrode 42 is also placed in contact with test solution 40. Both electrode 20 and electrode 42 are connected to a high input impedance electrometer or voltmeter. Electrode 42 is typically the usual conventional calomel mercury pool reference electrode with a controlled leak 44. In operation, a reference potential develops between reference electrode 42 and test solution 40, at an independently fixed value. A measurement potential develops across membrane 24 between the contact wire 32 and test solution 40. The total potential, $E_T$, measured by the voltmeter varies only in accordance with the measurement potential developed across membrane 24, thus indicating the presence and extent of activity of halide ions in solution 40.

The advantages of the electrodes of the present invention can be seen by reference to the following examples.

EXAMPLES

Figure 4A:
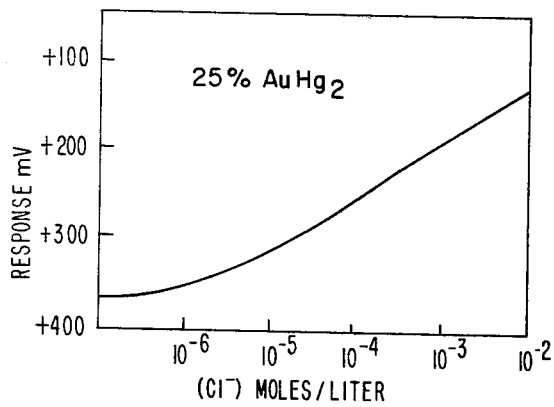
FIGS. 4a, b, c, d, e, f, 5a, b, c, d, e, f, 6a, and 6b are semi-logarithmic graphs showing the response to chloride ion of several different electrodes of different membrane composition, each such electrode made according to the present invention.

FIGS. 4a,-f, 5a-f, 6a and b, 7a-c and 8a and b display calibration curves for the various electrodes produced according to the present invention, further detailing the advantages of the new and improved structure.

FIGS. 4a-f and 6a and b illustrated collectively fourteen different compositions of the mercurous chloride-mercury gold amalgam mixture.

Figure 7A:
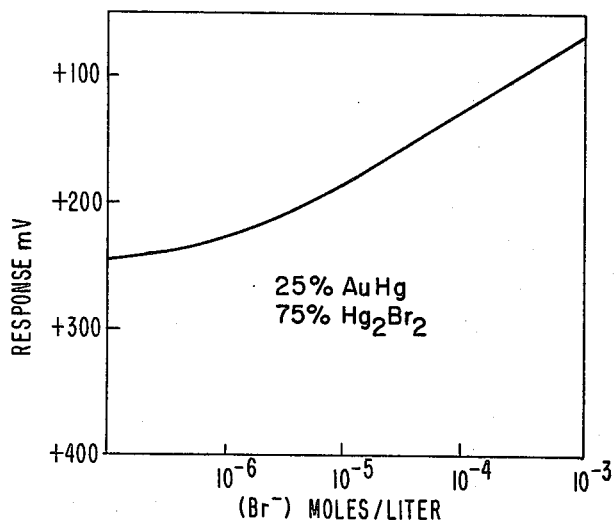
FIGS. 7a-c are semi-logarithmic graphs showing the response to bromide ion of several different electrodes each made according to the present invention.
Figure 7B:
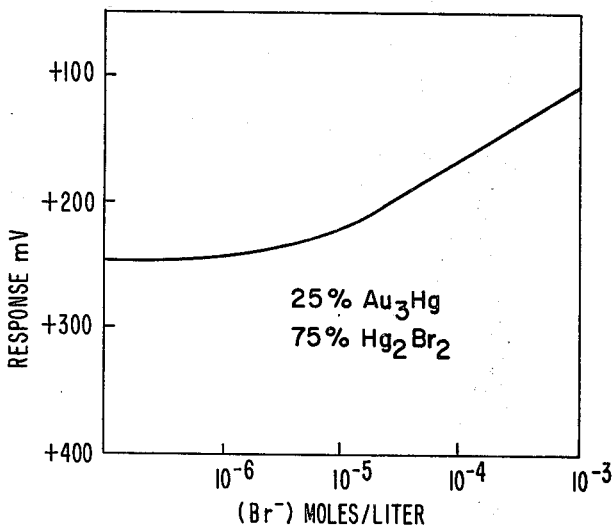
Figure 7C:
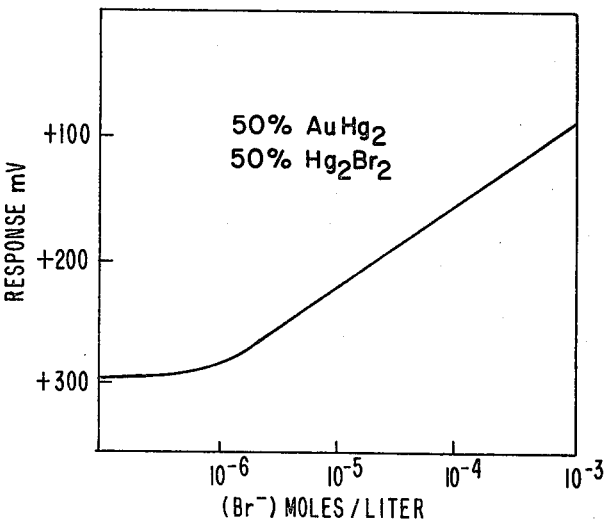

FIGS. 7a-c illustrate three representative calibration curves for the bromide ion sensitive amalgam electrode mixture, further demonstrating the versatility of the claimed invention.

Figure 8A:
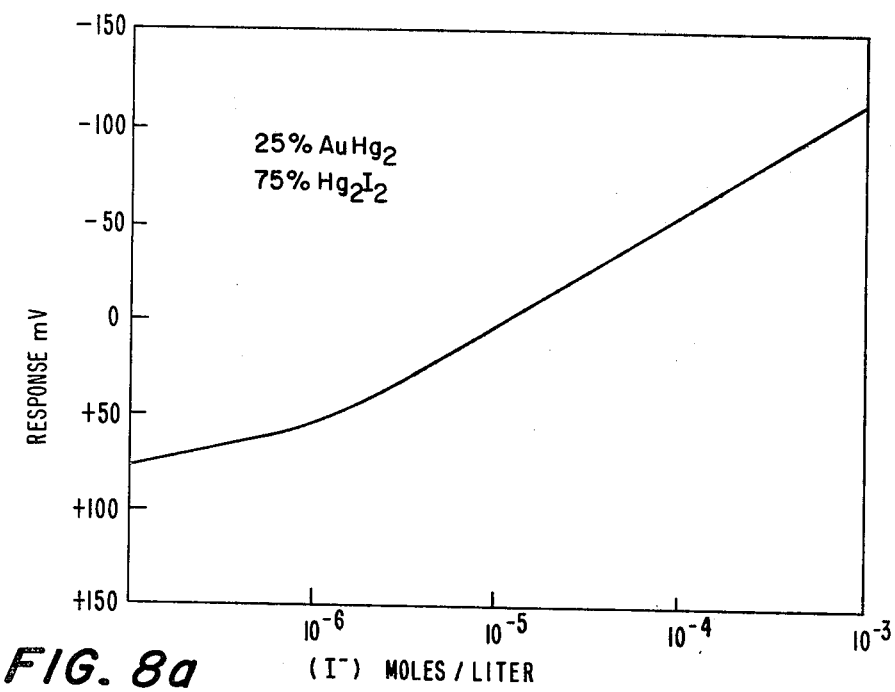
FIGS. 8a and 8b are semi-logarithmic graphs showing the response to iodide ion of several different electrodes each made according to the present invention.

FIGS. 8a and b illustrate two representative calibration curves for the iodide ion sensitive amalgam electrode mixture.

EXAMPLE I

More particularly, FIGS. 4a-f demonstrate the effect of a change in the amalgam component of the mixture. In FIGS. 4A through 4F, the mixture is composed of 75% by volume mercurous chloride, $Hg_2Cl_2$. It is the amalgam component that is altered in the various calibration curves shown. The response is shown on the ordinate in millivolts. The concentration of chloride ion, $Cl^-$, is shown on the abscissa, which is also a logarithmic axis.

Figure 3:
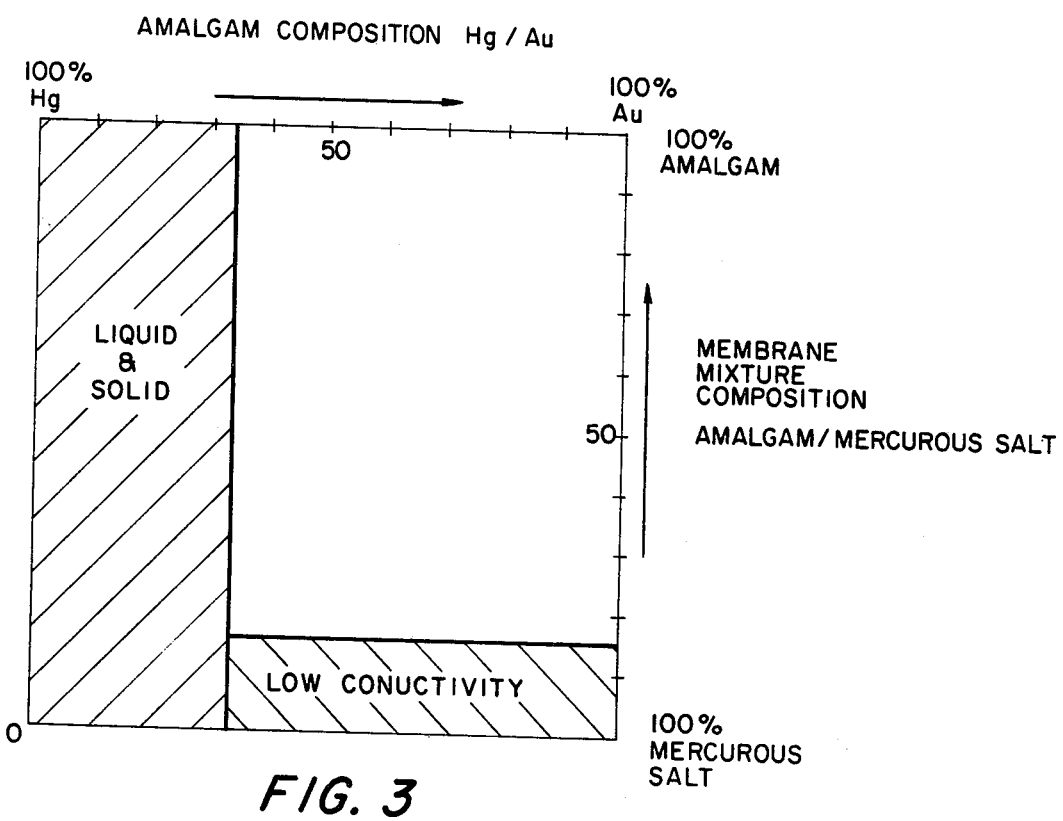
FIG. 3 is a chart indicating the range of acceptable compositions of membrane materials, more fully described below.
Figure 9:
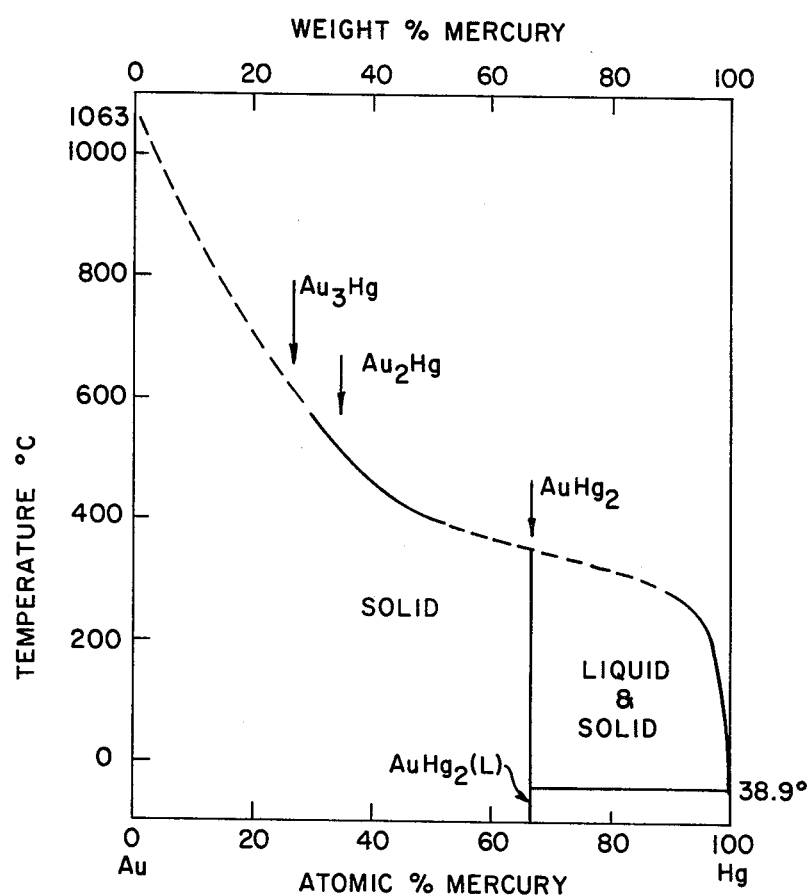
FIG. 9 is a phase diagram showing the solubility of mercury, Hg, in solid gold, Au.

As FIG. 4A shows, for an electrode composed with 25% by volume $AuHg_2$, i.e., two parts of mercurous to one part of gold, the millivolt response to changes in chloride ion concentration is approximately linear from a minimum detectable chloride ion concentration at the "mud" level of $10^{-7}$ moles/liter. The electrode provides excellent linear response to $10^{-2}$ moles/liter in the typical Nernstian fashion. The $AuHg_2$ composition is near the limiting lowest ratio of gold to mercury possible, as FIG. 9 illustrates and FIG. 3 summarizes, since any lower ratio results in a liquid-solid mixture which, when pressed at excessive pressures returns to the liquidous curve composition of the phase diagram in FIG. 9. By claiming the range of ratios from 33/67 to essentially 100/0, it is intended to include the full range of mercury-gold amalgam which coexist as a solid with the mercurous halide salt, in whatever percentage of ratios. It is believed that although a mixture can be prepared which would contain a higher relative amount of mercury in the amalgam, upon pressing, this excess of mercury is removed according to the phase diagram of FIG. 9, and the effective limiting ratio is 33/67.

Figure 4B:
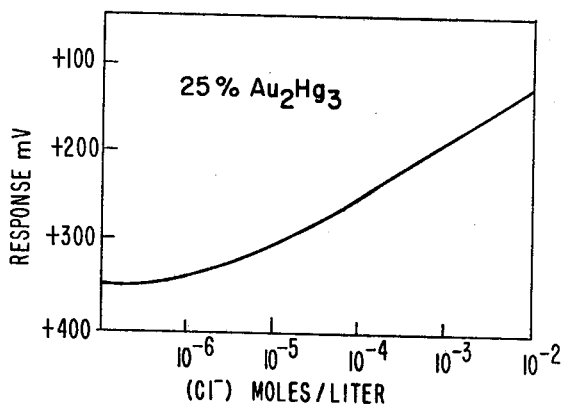

FIG. 4B shows a calibration curve where the gold/mercury ratio in the amalgam is 40/60. A response curve is shown analagous to that for the 33/67 composition.

Figure 4C:
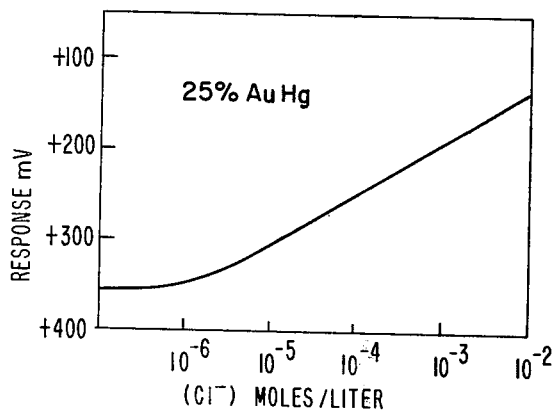
Figure 4D:
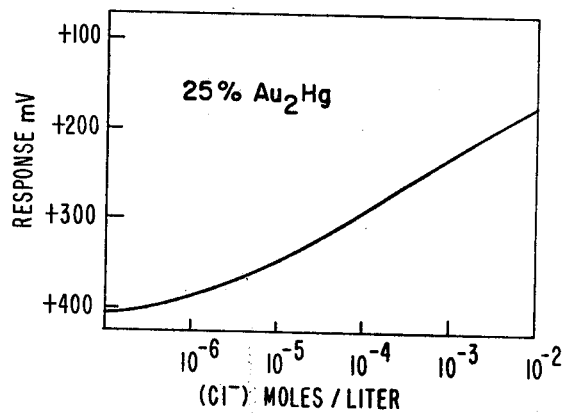
Figure 4E:
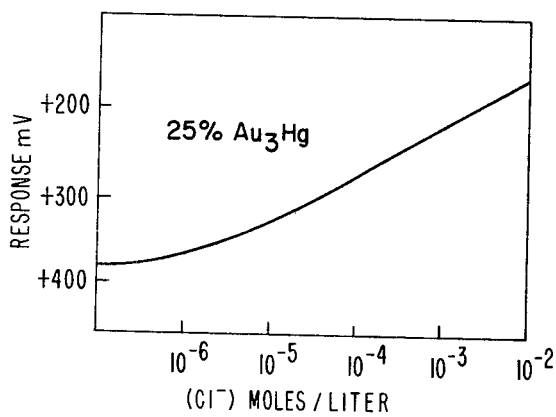

FIG. 4C shows a calibration curve where the ratio in the amalgam is 50/50. In FIG. 4D, the ratio 67/33. In FIG. 4E, the ratio is 75/25.

Figure 4F:
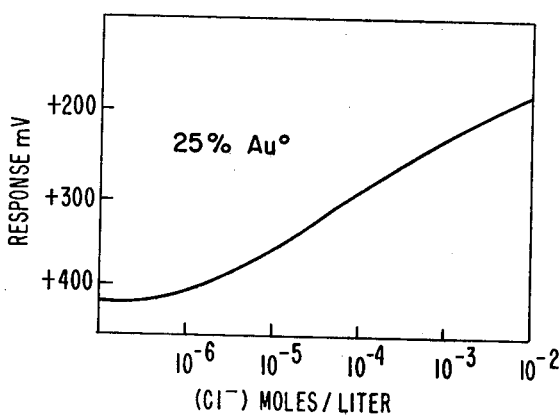

The curve in FIG. 4F shows response when the amalgam is essentially pure gold. Interestingly, the response is analogous to the compositions in FIGS. 4A-4E. A description of the manufacture of a typical membrane pellet of this composition will further describe the practice of the present invention.

The membrane is manufactured as follows:

Since the end composition of the membrane is to be 75% calomel ($Hg_2Cl_2$) by volume and 25% gold an arbitrary amount of end product of calomel, 0.004 moles, is selected. Since this amount of calomel weighs 1.888 g and the density of the calomel is 7.15 g/cc, the volume of the calomel is 0.264 cc. This is 75% of the total powder volume so the volume of the gold is desired to be 0.088 cc. Since the density of gold is 19.3 g/cc, 0.0086 moles of gold is required to obtain the desired mixture.

To 500 ml of water are added, in order 20 ml of 1 M HCl, 19.2 ml of 0.208 M $Hg_2(ClO_4)_2$ or 0.004 moles, 0.0086 moles of $HAuCl_4 \cdot 3H_2O$, and 13.9 ml of 1.86 M $CrCl_2$ or 0.0258 moles. The solution is being constantly stirred throughout addition and reaction. The mercurous perchlorate is altered to calomel providing 0.004 moles, and chromous chloride reduces chloroauric acid to form pure gold, $Au^0$. Upon washing and pressing the resultant precipitate, the membrane of FIG. 4F is formed.

Note that the addition of more reducing agent $CrCl_2$ would result in reduction to mercury from calomel. By adjusting the various amounts of components, the ratio of gold/mercury in the amalgam may be altered to a different value. Similarly, the ratio of amalgam to calomel is altered.

The resulting powder is stirred and then washed with four liters of $10^{-2}$ M HCl and 0.5 liters of MeOH. After drying as described above, the powder is pressed into the membrane form and shape.

EXAMPLE II

FIGS. 5a-f show calibration curves for various electrodes wherein the mixture is altered in the ratio of amalgam to mercurous chloride. Ratios vary from 15/85 to essentially 100/0. As the curves in FIGS. 5a-f amply illustrate, excellent response to changes in chloride ion activity is shown over the same range.

Figure 5A:
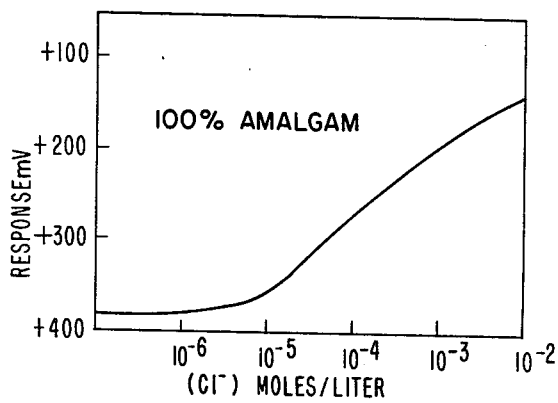

FIG. 5A shows the Nernstian response of an essentially pure amalgam electrode.

Figure 5B:
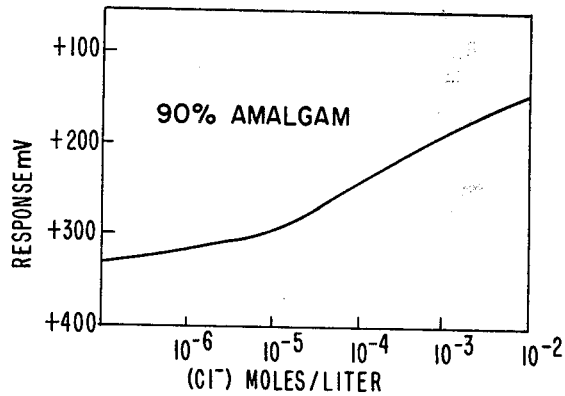

FIG. 5B shows the Nernstian response of an electrode where the membrane is composed of 10% mercurous chloride and 90% AuHg amalgam.

Figure 5C:
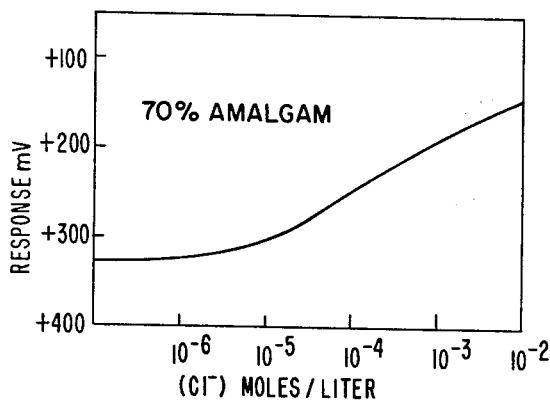

FIG. 5C shows the Nernstian response of an electrode where the membrane is composed of 30% mercurous chloride and 70% AuHg amalgam.

Figure 5D:
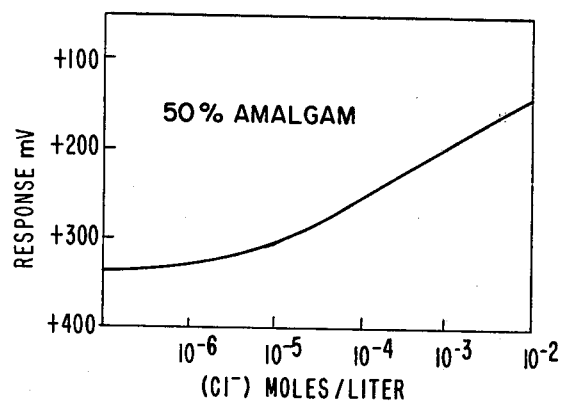
Figure 5E:
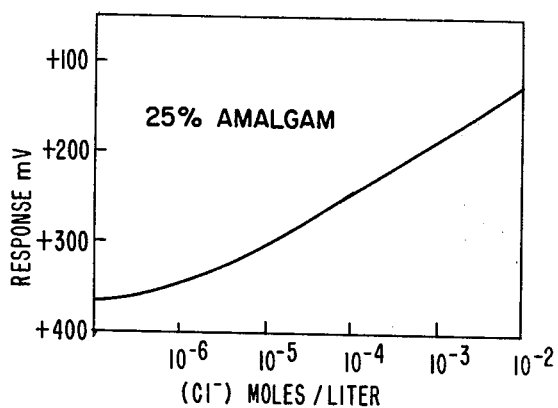

In FIG. 5D the membrane composition is 50% calomel/50% amalgam. In FIG. 5E the composition is 75% calomel and 25% amalgam.

Figure 5F:
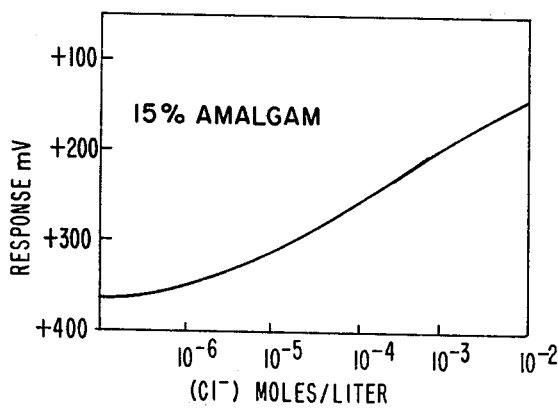

In FIG. 5F a 15/85 membrane response curve is shown. Nernstian response is again observed. Although a lower ratio of amalgam to calomel is possibly obtained and has been carried out in the laboratory, the non-conductive nature of these mixtures make their use impractical, especially in light of the high performance of the above compositions.

EXAMPLE III

Shown in FIGS. 6a and 6b are two further examples of possible calomel amalgam compositions. The FIG. 6A composition is a variant on that of FIG. 5A, the only change being in the makeup of the amalgam. Good response is observed over the same range of chloride ion concentration.

FIG. 6B shows the response of an electrode containing a membrane composed of $37\frac{1}{2}\%$ $AuHg_2$ and $62\frac{1}{2}\%$ $Hg_2Cl_2$. This mixture is believed to be a typical production composition. Response is again typical Nernstian.

EXAMPLE IV

FIGS. 7a-c present three representative curves showing response to bromide ion where the mercurous salt is $Hg_2Br_2$. The compositions shown are typical mixtures. The range of possible mixtures is as described for the chloride ion sensitive membranes. Nernstian response is also observed.

EXAMPLE V

Figure 8B:
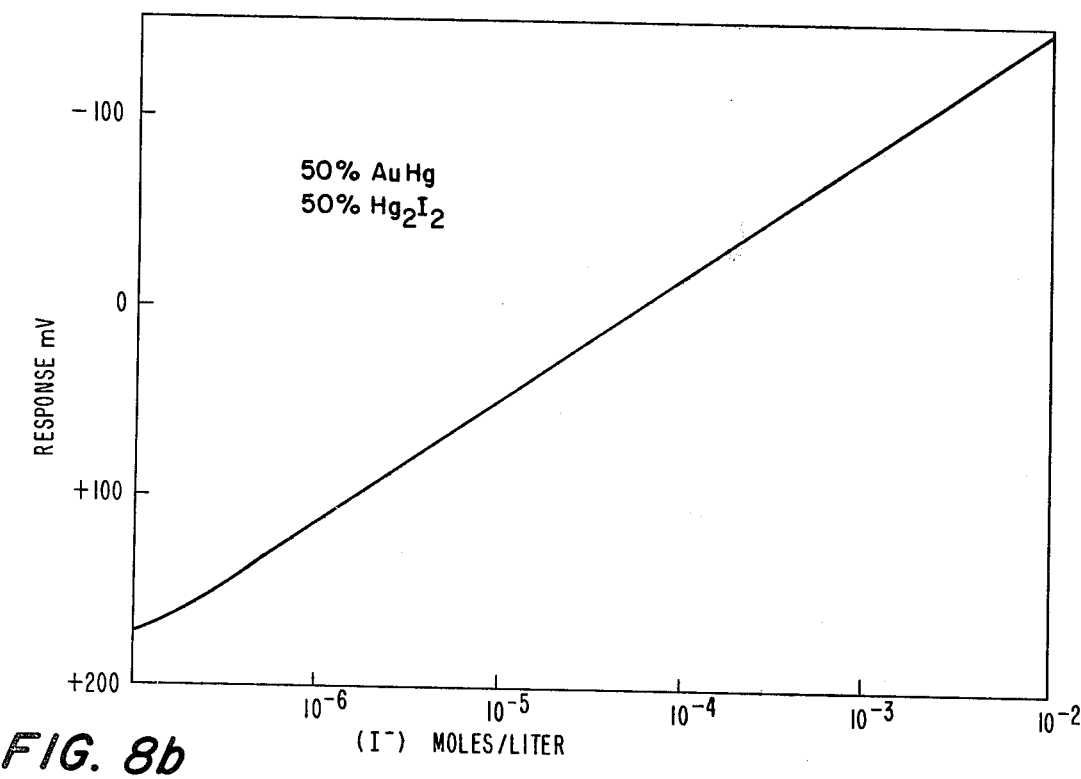

FIGS. 8a and 8b present two representative curves showing response to iodide ion when the mercurous salt is $Hg_2I_2$. The compositions shown are typical mixtures. The range of possible mixtures is as described by the chloride ion sensitive membranes. Nernstian response is also observed.

Other mercurous salts would result in membranes sensitive to other anions when mixed with a mercury-gold amalgam provided first that the anion of the salt does not form extensive complexes with the other membrane components and second that the solubility product of the salt is low enough to be of practical interest. Examples of such mercurous salts are those formed with the following anions:

Thiocyanate: $SCN^-$
Oxalate: $C_2O_4^{-2}$
Selenate: $SeO_3^{-2}$
Sulfide: $S^{-2}$
Tungstate: $WO_4^{-2}$
Molybdate: $MoO_4^{-2}$
Quinaldate: $Q^{-2}$ Since various changes may be made in the above description without departing from the scope of the present invention, it is intended that all matter contained in the above description, the drawings, and claims, shall be interpreted in an illustrative and not a limiting sense.

What is claimed is:

1. An electrochemical electrode sensitive to halide ion $X^-$ in solution and comprising:
    a substantially imporous membrane composed of a mixture of a solid amalgam of gold and mercury with a finely divided mercurous halide salt in the form $Hg_2X_2$; and
    means for forming an electrical contact with one surface of said membrane at a substantially fixed potential.

2. An electrode as defined in claim 1 sensitive to chloride ion wherein said salt is mercurous chloride, $Hg_2Cl_2$.

3. An electrode as defined in claim 1 sensitive to bromide ion wherein said salt is mercurous bromide, $Hg_2Br_2$.

4. An electrode as defined in claim 1 sensitive to iodide ion wherein said salt is mercurous iodide, $Hg_2I_2$.

5. An electrode as defined in claim 1 wherein the ratio of gold to mercury in the amalgam lies within the range of 33/67 to essentially 100/0.

6. An electrode as defined in claim 1 wherein the ratio of amalgam to the salt in the mixture lies within the range of 15/85 to essentially 100/0.

7. An electrode as defined in claim 1 wherein said means for forming an electrical contact comprises a wire embedded in a conductive carbon epoxy placed on the interior surface of the membrane.

8. A method for producing an ion-sensitive membrane for an electrochemical electrode comprising the steps of:
    intimately mixing a solid amalgam of gold and mercury with a finely divided mercurous halide salt selected from the group consisting of mercurous chloride, mercurous bromide, and mercurous iodide; and
    compressing said mixture with sufficient force to render it a substantially imporous mass.

9. A method as defined in claim 8 wherein said step of intimately mixing comprises:
    co-precipitating said gold, mercury, and mercurous halide in a common solution;
    washing the co-precipitate sufficiently to remove substantially all contaminants; and
    drying the washed co-precipitate.

10. A method as defined in claim 8 wherein said mixture is compressed under pressures above 10,000 p.s.i.

11. A method of producing an electrochemical electrode sensitive to halide ions in solution comprising the steps of:
    intimately mixing a solid amalgam of gold and mercury with a finely divided mercurous halide salt selected from the group consisting of mercurous chloride, mercurous bromide, and mercurous iodide;
    compressing said mixture with sufficient force to render it a substantially imporous mass;
    forming a membrane from said mass; and
    forming an electrical contact with one surface of said membrane at a substantially fixed potential.

* * * * *